United States Patent [19]
Chen

[11] Patent Number: 6,149,611
[45] Date of Patent: Nov. 21, 2000

[54] FOOT MASSAGER

[76] Inventor: Kim-Chu Chen, No. 200, Yung-Ta Rd., Yung-Kang City, Tainan Hsien, Taiwan

[21] Appl. No.: 09/293,917

[22] Filed: Apr. 19, 1999

[51] Int. Cl.[7] ........................................................ A61H 7/00
[52] U.S. Cl. .............................. 601/22; 601/15; 601/50; 601/70; 601/112
[58] Field of Search ..................... 601/15, 18, 22, 601/28, 29, 30, 31, 32, 50, 51, 56, 64, 65, 66, 70, 78, 85, 86, 87, 104, 112

[56] References Cited

U.S. PATENT DOCUMENTS

| | | | |
|---|---|---|---|
| 2,490,074 | 12/1949 | Marty | 601/18 |
| 2,553,873 | 5/1951 | Schwebel | 601/20 |
| 4,446,855 | 5/1984 | Friedson | 601/15 |
| 5,099,826 | 3/1992 | Hayakawa | 601/61 |
| 5,573,500 | 11/1996 | Katsunuma | 601/111 |
| 5,716,331 | 2/1998 | Chang | 601/50 |
| 5,785,668 | 7/1998 | Nobuzi | 601/50 |
| 5,797,859 | 8/1998 | Prehodka | 601/22 |
| 5,827,205 | 10/1998 | Iwamoto | 601/78 |
| 5,868,688 | 2/1999 | Avidor et al. | 601/87 |
| 5,910,123 | 6/1999 | Wang | 601/50 |

*Primary Examiner*—Danton D. DeMille
*Assistant Examiner*—Benjamin Koo
*Attorney, Agent, or Firm*—Dougherty & Troxell

[57] ABSTRACT

A foot massager, which includes a casing, a massaging disk supported on elastic blocks inside the casing, two massaging foot plates suspended in respective foot recesses at the massaging disk, a plurality of infrared light emitting devices respectively installed in the foot recesses below the massaging foot plates, a motor mounted in the casing and controlled to rotate two massaging plates through a worm and two gear meshed with the worm at two opposite sides, and a weight fastened to the motor shaft of the motor to increase the amplitude of vibration.

2 Claims, 4 Drawing Sheets

FOOT MASSAGER

BACKGROUND OF THE INVENTION

The present invention relates to a massaging apparatus, and more particularly to a foot massager for massing the sole of the foot.

FIG. 1 shows a foot massager according to Taiwan Patent Publication No. 76210302, issued on Feb. 1, 1989. This structure of foot massager comprises a housing 1, a motor 10 mounted inside the housing 1, an eccentric shaft 11 coupled to the motor 10 and extended out of a hole at the top side of the housing 1, a bearing 12 mounted on the eccentric shaft 11 outside the housing 1, a massaging disk 13 supported on the bearing 12, and spring members 4 connected between the massaging disk 13 and support means inside the housing 1. When the eccentric shaft 11 is rotated by the motor 10, the massaging disk 13 is forced to vibrate horizontally, and to rub against the sole of the foot placed on it. Because the bearing 12 and the motor 10 receive the weight of the foot, the bearing 12 and the motor 10 wear quickly with use. Further, because the massaging disk 13 is simply vibrated in horizontal direction, less massaging effect is achieved.

SUMMARY OF THE INVENTION

The present invention provides a foot massager which eliminates the aforesaid drawbacks. According to one aspect of the present invention, the foot massager uses a fixed foot massaging disk and two rotary massaging plates to rub the feet. According to another aspect of the present invention, infrared light emitting devices are installed in the fixed foot massaging disk, and controlled to emit light for stimulating the circulation of blood. According to still another aspect of the present invention, a worm and gear transmission mechanism is provided to transmit driving power from a motor to the rotary massaging plates. Because the motor does not directly receive the pressure from the user's feet, it service life is relatively prolonged.

DETAILED DESCRIPTION OF THE PREFERRED EMBODIMENT

Figure 1:
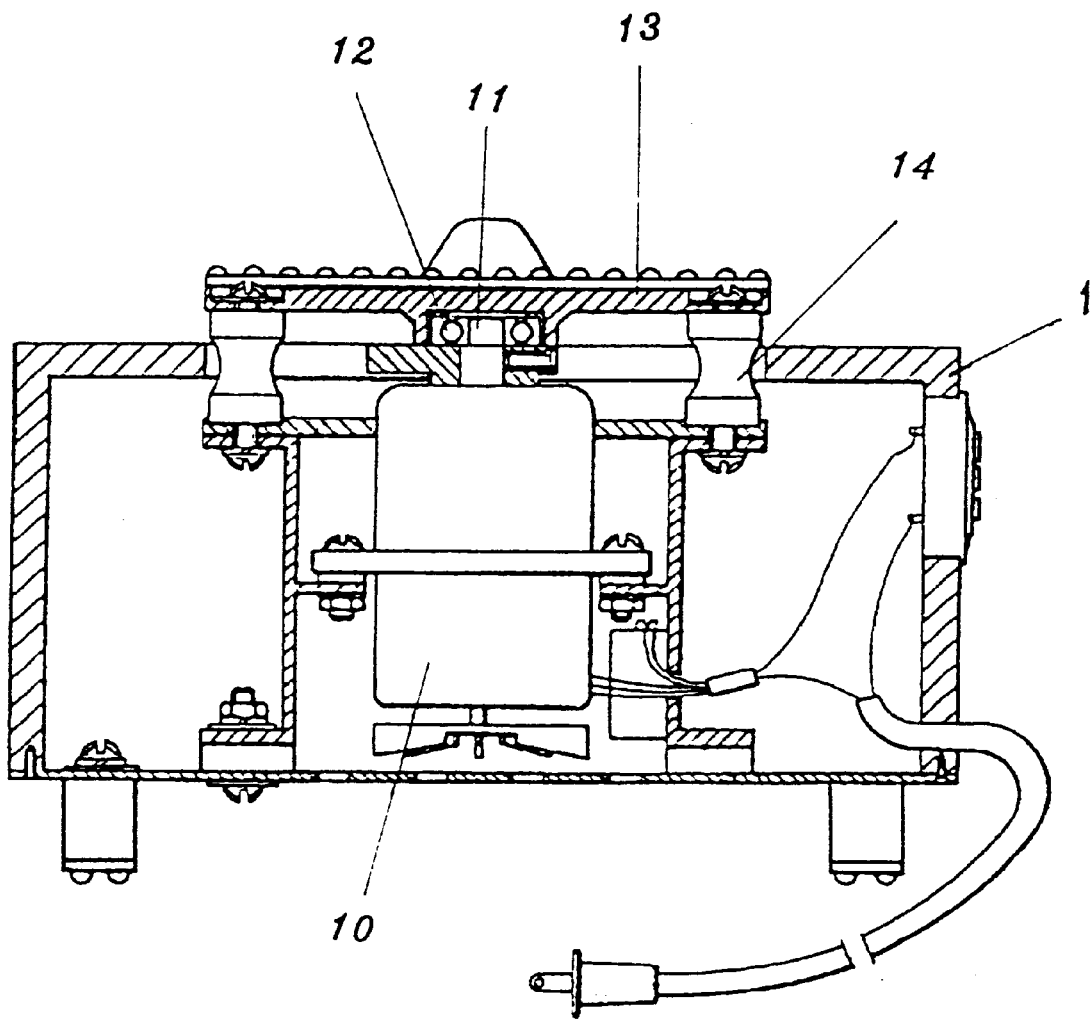
FIG. 1 is a sectional view of a foot massager according to the prior art.
Figure 2:
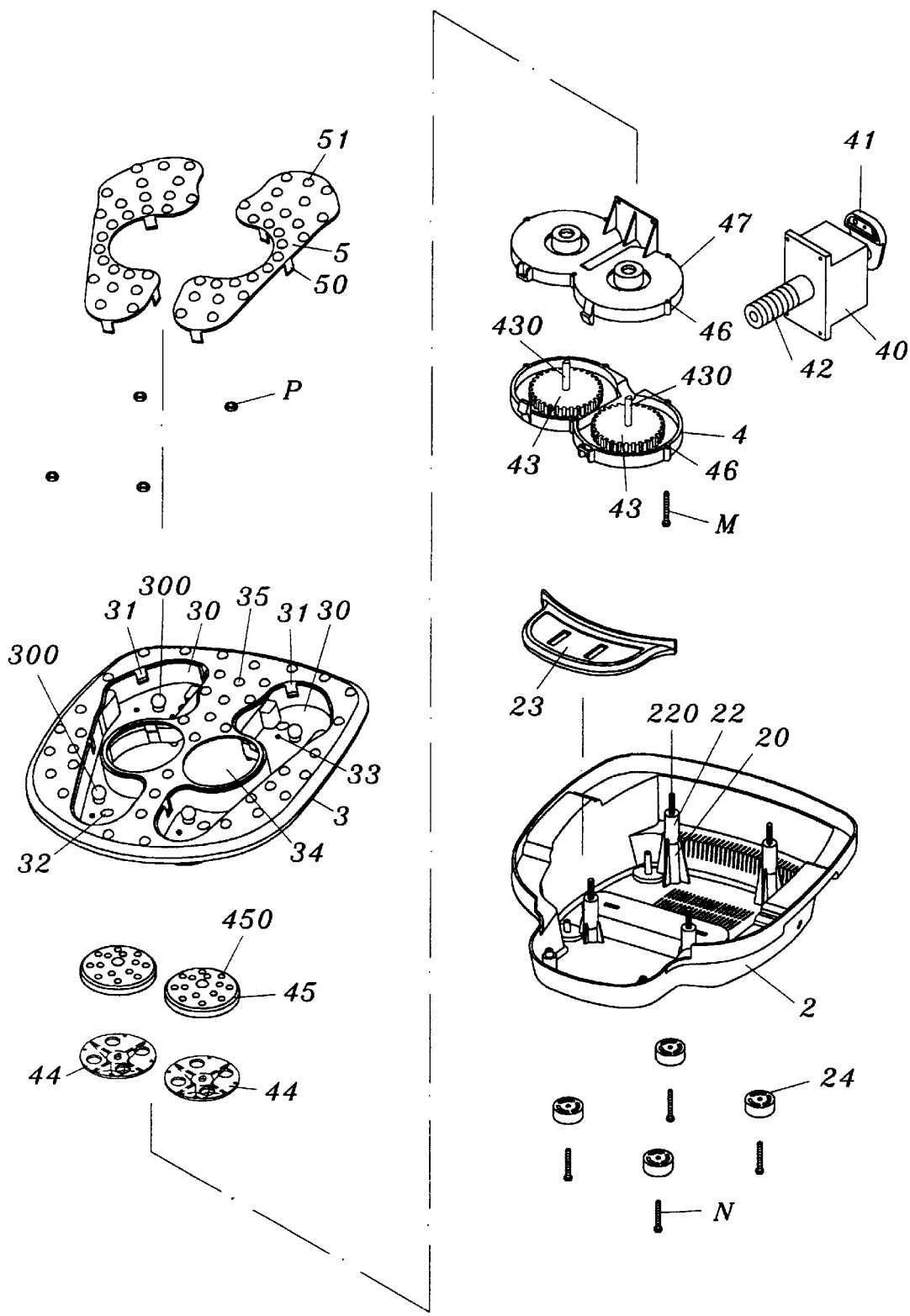
FIG. 2 is an exploded view of a foot massager according to the present invention.
Figure 3:
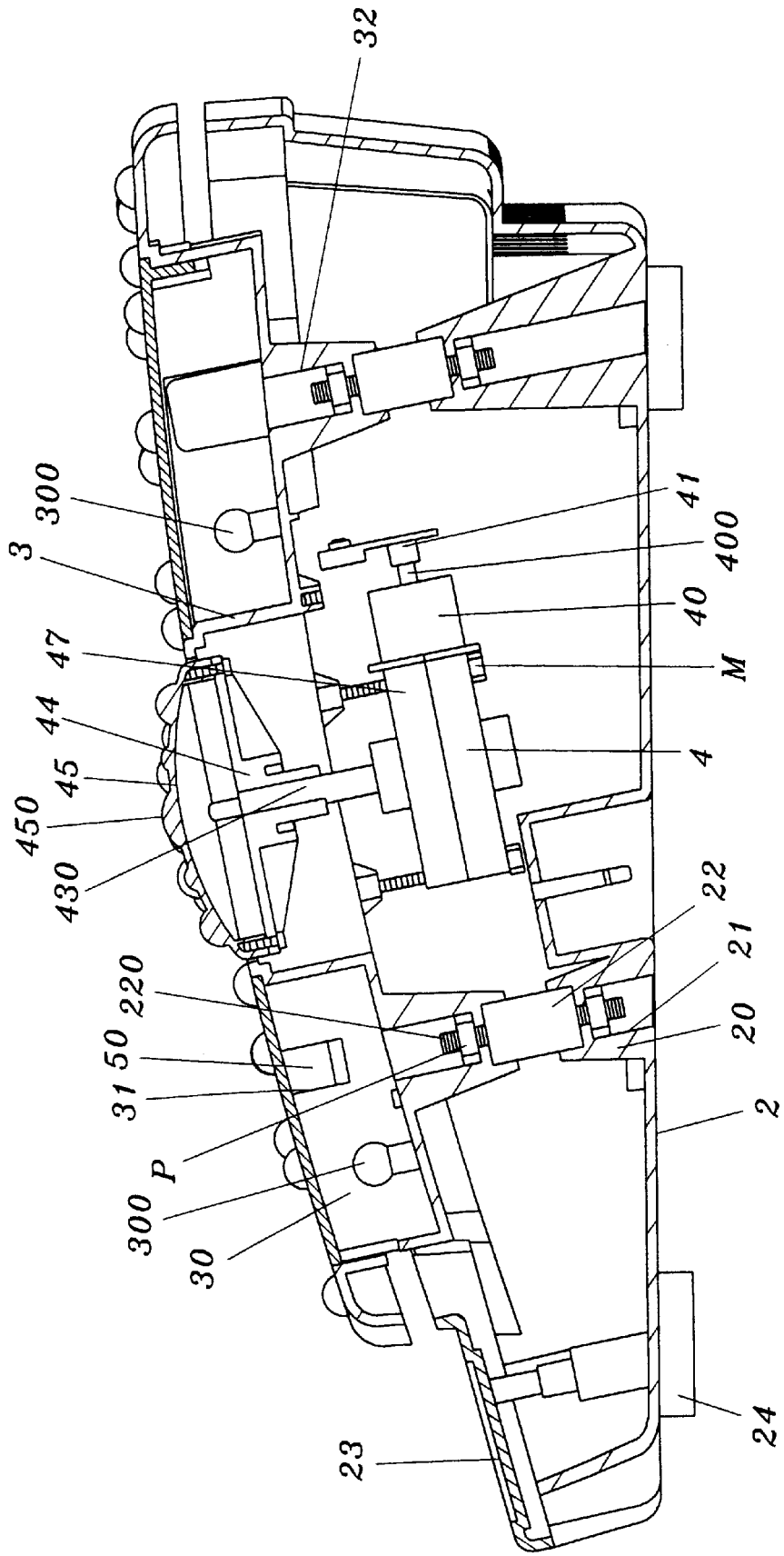
FIG. 3 is a sectional assembly view in an enlarged scale of the foot massager shown in FIG. 2.

Referring to FIGS. 2 and 3, a foot massager is shown comprising a casing 2. The casing 2 comprises four upright supports 20 disposed on the inside in four corners. Each upright support 20 defines an axial hole 21, which passes through the bottom side wall of the casing 2. An elastic block 22 is respectively mounted on each upright support 20 at the top and fastened to the respective axial hole 21. A screw rod 220 is axially connected to the elastic block 22 at each upright support 20 at the top. A power switch panel 23 is provided at the casing 2 at the top. Four shock absorbing foot members 24 are respectively fastened to the casing 2 in four corners at the bottom side by for example screws N. A massaging disk 3 is supported on the casing 2. The massaging disk 3 comprises two foot recesses 30, a plurality of raised portions 35 raised from the top side wall thereof around the foot recesses 30, a plurality of infrared light emitting diodes 300 respectively mounted in the foot recesses 30, a plurality of locating holes 31 spaced around the periphery of each of the foot recesses 30, a plurality of through holes 32 in the foot recesses 30 corresponding to the screw rods 220 at the elastic blocks 22 in the casing 2, a plurality of screw holes 33 in the foot recesses 30, and two round holes 34 spaced between the foot recesses 30. A motor holder 4 is fixedly mounted inside the casing 2 below the massaging disk 3, and covered with a cover plate 47. A motor 40 is fastened to the motor holder 4 at a back side within the casing 2. A weight 41 is coupled to the rear end of the motor shaft 400 of the motor 40. A worm 42 is fastened to the front end of the motor shaft 400 of the motor 40, and meshed between two gears 43, which are mounted inside the motor holder 4. The gears 43 each have a gear shaft 430 respectively extended out of a respective hole at the cover plate 47. Two massaging plate holders 44 are respectively fixedly fastened to the gear shafts 430 of the gears 43 to hold a respective massaging plate 45, which comprises a plurality of raised portions 450 raised from the top side wall thereof for massaging. Screw holes 46 are provided at the motor holder 4 and the cover plate 47, and respectively fastened to the screw holes 33 at the massaging disk 3. Two transparent massaging foot plates 5 are respectively mounted in the foot recesses 30 in the massaging disk 3. The massaging foot plates 5 each comprise a plurality of raised portions 51 at the top for massaging, and a plurality of downward hooks 50 respectively hooked in the locating holes 31 at the massaging disk 3.

Figure 4:
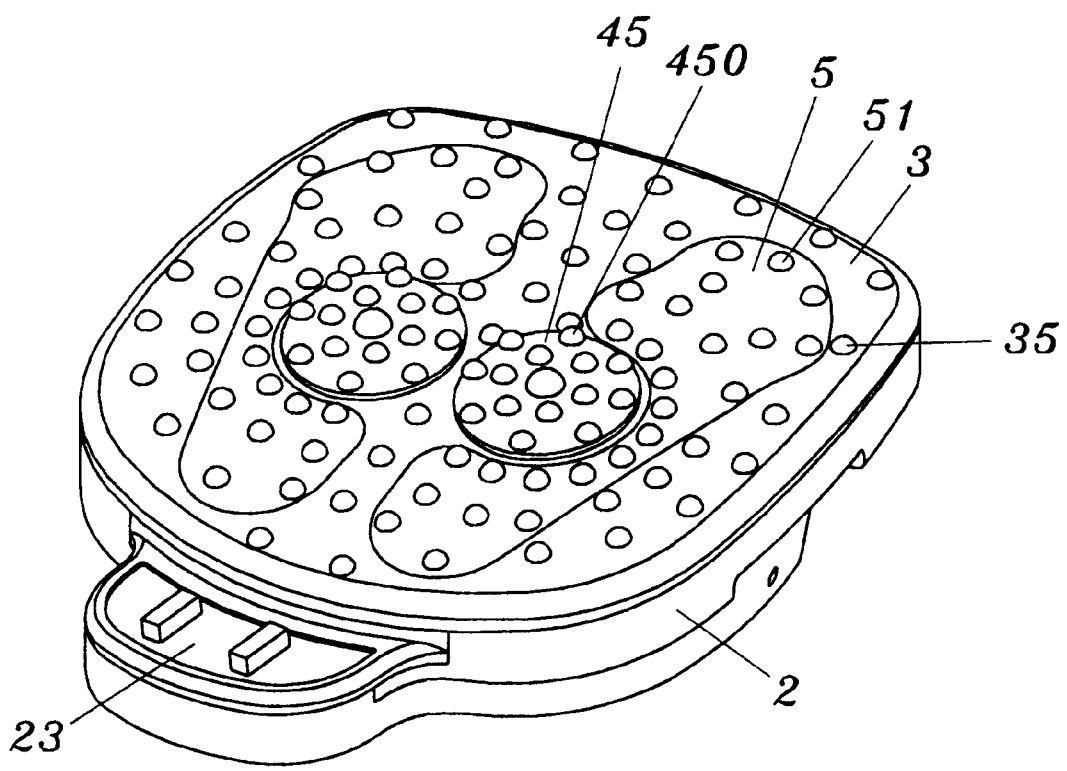
FIG. 4 is a perspective view of the foot massager according to the present invention.

The assembly process of the present invention is outlined hereinafter with reference to FIG. 4 and FIG. 3 again. The screw holes 46 at the motor holder 4 and the cover plate 47 are respectively fastened to the screw holes 33 at the massaging disk 3 by respective screws M, then the massaging disk 3 is supported on the elastic blocks 22 within the casing 2, enabling the screw rods 220 of the elastic blocks 22 to be respectively inserted through the through holes 32 at the massaging disk 3 and the massaging plate holders 44 with the respective massaging plates 45 to be suspended in the round holes 34 at the massaging disk 3, and then screw nuts P are respectively threaded onto the screw rods 220 to fix the massaging disk 3 to the casing 2, and then the massaging foot plates 5 are respectively mounted in the foot recesses 30 secured by hooking the downward hooks 50 of the foot plates 5 in the respective locating holes 31 at the massaging disk 3.

Referring to FIGS. 3 and 4 again, because the weight 41 is rotated with the motor shaft 400 during operation of the motor 40, the amplitude of vibration of the motor holder 4 is relatively increased. Because the massaging disk 3 is supported on the elastic blocks 22, the amplitude of vibration of the massaging disk 3 is relatively increased when vibrating waves are transmitted through the elastic blocks 22 to the massaging disk 3. When starting the motor 40, the infrared light emitting diodes 300 are turned on to emit infrared light through the transparent massaging foot plates 5 to heat the sole of the foot, causing the circulation of blood to be stimulated. Further, during the operation of the motor 40, the gears 43 are rotated by the worm 42 in reversed directions, therefore the massaging plates 45 are respectively rotated with the gear shafts 430 of the gears 43 to rub against the sole of each of the feet put on the massaging foot plates 5.

What is claimed is:

1. A foot massager comprising a casing, said casing comprising four upright supports disposed on the inside in four corners, four elastic blocks respectively mounted on said upright supports, said upright supports each comprising a screw rod vertically disposed at a top side, a power switch panel at a top side thereof, and four shock absorbing foot members at a bottom side thereof in four corners; and a massaging disk covered on said casing and supported on said elastic blocks, said massaging disk comprising four through holes respectively fastened to the screw rods at said elastic blocks by respective nuts, and a plurality of raised portions raised from a top side wall thereof for massaging;

wherein said massaging disk comprises two foot recesses, a plurality of infrared light emitting devices respectively mounted in said foot recesses and controlled to emit infrared light, a plurality of locating holes spaced around the periphery of each of said foot recesses, a plurality of screw holes in said foot recesses, and two round holes spaced between said foot recesses;

two foot plates are respectively mounted in said foot recesses in said massaging disk and suspended above said infrared light emitting devices, said massaging foot plates each comprising a plurality of raised portions at a top side thereof for massaging, and a plurality of downward hooks respectively hooked in the locating holes at said massaging disk;

two massaging plate holders are respectively rotated in the round holes in said massaging disk;

two massaging plates are respectively carried on said massaging plate holders and rotated with said massaging plate holders, said massaging plates each having a plurality of raised portions at a top side for massaging;

motor drive means installed in said casing to rotate said massaging plates, said motor drive means comprising a motor holder fixedly mounted inside said casing below said massaging disk, a cover plate covered on said motor holder, a motor fixedly fastened to said motor holder at a back side within said casing, said motor comprising a motor shaft, a weight fixedly fastened to said motor shaft of said motor at one end outside said motor holder, a worm fixedly fastened to said motor shaft of said motor at one end remote from said weight and disposed inside said motor holder, two gears respectively mounted inside said motor holder and meshed with said worm at two opposite sides, said gears each having a gear shaft respectively connected to said massaging plate holders and driven by said motor through said worm to rotate said massaging plate holders, said motor holder and said cover plate having respective screw holes respectively fastened to said screw holes at said massaging disk by screw members.

2. The foot massager of claim 1 wherein said foot plates are transparent, and the shape of said foot plates and said foot recesses of said massaging disk fit the shape of the sole of the foot.

* * * * *